United States Patent [19]

Saitou et al.

[11] Patent Number: 5,523,473
[45] Date of Patent: *Jun. 4, 1996

[54] METHOD OF PRODUCING NAPHTHALENEDICARBOXYLIC ACIDS AND DIARYLDICARBOXYLIC ACIDS

[75] Inventors: Noboru Saitou, Takatsuki; Koichi Hirota; Ren Hasebe, both of Suita; Norimasa Okuda, Kyoto; Ikuyo Katsumi, Osaka, all of Japan

[73] Assignee: Nippon Shokubai Co., Ltd., Osaka, Japan

[*] Notice: The term of this patent shall not extend beyond the expiration date of Pat. No. 5,144,066.

[21] Appl. No.: 450,934

[22] Filed: May 25, 1995

Related U.S. Application Data

[63] Continuation of Ser. No. 998,745, Dec. 30, 1992, abandoned.

[51] Int. Cl.$^6$ .................................................. C07C 51/265
[52] U.S. Cl. ............................................. 562/416; 562/417
[58] Field of Search ..................................... 562/416, 417

[56] References Cited

U.S. PATENT DOCUMENTS

| | | | |
|---|---|---|---|
| 4,794,195 | 12/1988 | Hayashi et al. | 562/414 |
| 4,950,786 | 8/1990 | Sanchez et al. | 562/416 |
| 4,970,338 | 11/1990 | Matsuda et al. | 562/416 |
| 5,144,066 | 9/1992 | Saitou et al. | 562/416 |

FOREIGN PATENT DOCUMENTS

| | | |
|---|---|---|
| 48-27318 | 8/1973 | Japan . |
| 49-36702 | 10/1974 | Japan . |
| 52-77022 | 6/1977 | Japan . |
| 56-3777 | 1/1981 | Japan . |
| 57-16831 | 1/1982 | Japan . |
| 60-56694 | 12/1985 | Japan . |
| 61-140540 | 6/1986 | Japan . |
| 61-246144 | 11/1986 | Japan . |
| 62-106045 | 5/1987 | Japan . |
| 62-212345 | 9/1987 | Japan . |
| 63-63638 | 3/1988 | Japan . |
| 63-122645 | 5/1988 | Japan . |
| 63-310846 | 12/1988 | Japan . |
| 64-3148 | 1/1989 | Japan . |
| 1-121240 | 5/1989 | Japan . |
| 1-160943 | 6/1989 | Japan . |
| 1-287055 | 11/1989 | Japan . |
| 23777 | 1/1990 | Japan . |
| 2-32042 | 2/1990 | Japan . |
| 2-32041 | 2/1990 | Japan . |

OTHER PUBLICATIONS

English language abstract for JP 1–287055.
English language abstract for JP 1–160943.
English language abstract for JP 64–3148.
English language abstract for JP 62–212345, 1987.
English language abstract for JP 61–140540.
English Language Abstract for JP 60–56694, 1985.
English Language Abstract for JP 57–16831, 1982.
English Language Abstract for JP 56–3337, 1981.
English Language Abstract for JP 2–3777, 1981.
English Language Abstract for JP 63–310846, 1988.
English language abstract for 2–32042 1990.
English language abstract for 62–106045, 1987.
English language abstract for 63–122645, 1988.
English language abstract for 63–63638, 1988.
English language abstract for 2–32041, 1990.
"Oxidation Communications 3," Nos. 3–4, pp. 303–314 (1983).
"Oxidation of p,p'–Bitolyl," P. Lumumba Univ. of Int'l Friendship. Translated from Zhurnal Prikladnoi Khimii, vol. 40, No. 4, pp. 935–936, Apr., 1967.

*Primary Examiner*—José G. Dees
*Assistant Examiner*—Samuel Barts
*Attorney, Agent, or Firm*—Birch, Stewart, Kolasch & Birch

[57] ABSTRACT

A method of producing naphthalenedicarboxylic acids by the oxidation of dialkyl-substituted naphthalene with a gas containing molecular oxygen in an organic solvent and in the presence of a catalyst comprising copper and bromine, or a catalyst comprising copper, bromine and at least one kind of element/compound selected from the group of consisting of amine compounds and heavy metallic elements which are vanadium, manganese, iron, nickel, palladium and cerium. And a method of producing diaryldicarboxylic acids by the oxidation of dialkyl-substituted diaryl compounds with a gas containing molecular oxygen in an organic solvent and in the presence of the same catalyst. These methods permit high yields of naphthalenedicarboxylic acids of high purity and of diaryldicarboxylic acids of high purity with the use of small amounts of catalyst.

28 Claims, No Drawings

METHOD OF PRODUCING NAPHTHALENEDICARBOXYLIC ACIDS AND DIARYLDICARBOXYLIC ACIDS

This application is a continuation of application Ser. No. 07/998,745 filed on Dec. 30, 1992, now abandoned.

The present invention relates to a method for producing naphthalenedicarboxylic acids and diaryldicarboxylic acids by the oxidation of dialkyl-substituted naphthalene compounds and of dialkyl-substituted diaryl compounds with a gas containing molecular oxygen under liquid-phase conditions in an organic solvent.

BACKGROUND OF THE INVENTION

Conventionally, it is known that films and various by-products made of polyethylene naphthalate, which is formed by reacting 2,6-naphthalenedicarboxylic acid and ethylene glycol, have improved mechanical strength, heat-resistance, size stability etc. relative to those produced from polyethylene terephthalate which is formed from terephthalic acid.

As for the production of 2,6-naphthalenedicarboxylic acid (hereinafter referred to as 2,6-NDA), the following methods are known. (A) Methods of producing 2,6-NDA by the oxidation of dialkyl-substituted naphthalene with molecular oxygen in an acetic acid solvent in the presence of a catalyst comprising cobalt, manganese and bromine (Japanese Publication for Examined Patent applications No. 48-27318/1973, No. 56-3337/1981, Japanese Publication for Unexamined Patent applications No. 61-140540/1986, No. 62-212345/1987, No. 64-3148/1989, No. 1-160943/1989 and No. 1-287055/1989).

Meanwhile, for the production of aromatic carboxylic acids, (B) a method disclosed in Japanese Publication for Unexamined Patent Application No. 52-77022/1977 and (C) a method disclosed in Japanese Publication for Examined Patent Application No. 60-56694/1986 are known.

In methods (A), when the reaction is started, a large amount of catalyst in proportion to the starting material is required in order to repress the formation of undesirable by-products, including tar-like substances and naphthalene ring-scissioned by-products such as trimellitic acid, and additionally to improve the yield of 2,6-NDA. Consequently, complicated industrial processes are required in these methods in order to separate and recover the catalyst after the reaction. Moreover, in order to obtain 2,6-NDA of a high purity, a number of refining operations are necessary.

In method (B), it is disclosed that in producing terephthalic acid with a catalyst comprising cobalt, manganese and bromine in an acetic acid solvent, if a small amount (ppm) of copper is added to the acetic acid solvent, the oxidative decomposition of the acetic acid solvent is repressed. In this method, however, adding copper does not stimulate the catalytic reaction, and therefore it is hard to believe that copper contributes to the catalytic reaction. In method (C) for producing terephthalic acid with a catalyst comprising copper and bromine in a water solvent, the highest yield of terephthalic acid (molar yield) is around 70 percent, and again no statement on 2,6-NDA is disclosed in this application.

As is clear from the prior art, a method of producing 2,6-NDA from dialkyl-substituted naphthalene at a high yield has not yet been fully established.

Meanwhile, diaryldicarboxylic acids are important compounds as copolymer components for the manufacture of fibers, films, plasticizers, synthetic resins etc.

Conventionally, the production of the diaryldicarboxylic acids by the oxidation of starting material with molecular oxygen in an acetic acid solvent in the presence of a catalyst comprising cobalt, manganese and bromine is known. For this kind of method, for instance, the following four methods are known: (1) A method of producing diaryldicarboxylic acids by the oxidation of 4,4'-dimethylbiphenyl (see Zh. Prikl. Khim.40 (4), 935-6 (1967)); (2) A method of producing diaryldicarboxylic acids by the oxidation of 4,4'-dimethylbiphenyl (see Japanese Publication for Unexamined Patent Applications No. 2-32041/1990 and No. 63-63638/1988); (3) A method of producing diaryldicarboxylic acids by the oxidation of 4,4'-diisopropylbiphenyl (see Japanese Publication for Unexamined Patent Application No. 63-122645/1988); and (4) A method of producing diaryldicarboxylic acids by the oxidation of 4,4'-dicyclohexylbiphenyl (see Japanese Publication for Unexamined Patent Application No. 57-16831/1982).

Also, (5) Japanese Publication for Unexamined Patent Application No. 63-310846/1988 discloses a method of producing various kinds of diaryldicarboxylic acids in the presence of the above-mentioned catalyst.

However, these methods present the following drawbacks. In method (1), 4,4'-biphenyldicarboxylic acids can be obtained at 79 mole percent yield by oxidizing 4,4'-dimethylbiphenyl with a catalyst comprising cobalt, manganese and bromine in an acetic acid solvent. However, the amount of the high-cost cobalt catalyst required is equivalent to 20 weight percent of the amount of the starting material, thereby resulting in a high production cost. Besides, 79 mole percent yield is not high enough.

In method (2), the reaction is carried out in an acetic acid solvent in the presence of a catalyst comprising cobalt, manganese and bromine, in order to obtain 4,4'-biphenyldicarboxylic acid at a high yield of at least 80 mole percent. However, since the amount of the high-cost cobalt catalyst required is equivalent to 15 weight percent of the amount of a substrate, this method also results in a high production cost.

In method (3), the reaction is carried out in an acetic acid solvent in the presence of a catalyst comprising cobalt, manganese and bromine equivalent to at least 15 weight percent of the amount of the starting material. This method achieves only a low yield of 35.8 mole percent.

In method (4), the reaction is carried out in the presence of a catalyst comprising similar catalyst components to the catalysts in methods (1), (2), (3), whose weight ratio to the starting material is at least 30 percent. However, this method also results in a low yield of 40 mole percent.

In method (5), diaryldicarboxylic acids are produced at a high yield of at least 90 mole percent by oxidizing various kinds of dialkyl-substituted diaryl compounds in the presence of a catalyst whose essential components are cobalt and bromine. However, the present inventors examined this method and found that the products had dark color. The following two reasons are listed for this cause: firstly, due to the cobalt catalyst; and secondly, the formation of large amounts of by-products which easily to color and of tar-like substances. Moreover, since the high-cost cobalt catalyst is essential in this method, industrially its production cost is not sufficiently low.

As aforesaid, in the above conventional methods, as large amounts of catalyst comprising high-cost cobalt catalyst are used, industrially sufficiently low production costs can not be achieved. Also, a method of producing diaryldicarboxylic acids having light color from the dialkyl-substituted diaryl compounds in the presence of the above-mentioned conventional catalysts with high yields of diaryldicarboxylic acids has not yet been established.

SUMMARY OF THE INVENTION

An object of the present invention is to provide a method of producing naphthalenedicarboxylic acids (NDA) efficiently by oxidizing dialkyl-substituted naphthalene under liquid phase conditions.

Another object of the present invention is to provide a method of producing 2,6-naphthalenedicarboxylic acid of a high purity at a high yield from 2,6-diisopropylnaphthalene.

A further object of the present invention is to provide a method of producing light-colored diaryldicarboxylic acids from dialkyl-substituted diaryl compounds with an improved yield of diaryldicarboxylic acids by the use of a reduced amount of a new and low-cost catalyst compared with the conventional methods.

In order to achieve the above objects, the present inventors have studied various catalysts for use as oxidation catalyst in the method of producing 2,6-NDA, and found that, as disclosed in U.S. Pat. No. 5,144,066, a catalyst comprising copper and bromine and a catalyst comprising copper, bromine and heavy metal can permit high yields of 2,6-NDA having high purity by the use of reduced amounts of catalyst compared with the case of using a standard catalyst comprising cobalt, manganese and bromine.

Since the reaction has a high calorific value with the use of such catalysts, the way of eliminating heat is a very important matter in accelerating the reaction. In order to eliminate heat, it is effective to increase the latent heat of vaporization of an organic solvent accompanied by the air by raising the reaction temperature.

Experiments were performed by increasing the latent heat of vaporization of an organic solvent. The results show that, when the above catalysts were used, the recovery of the organic solvent was considerably lowered because of the combustion of the organic solvent. It is discovered through the experiments that, by further reducing the amount of copper in the catalysts, i.e., by increasing the atom ratio of other components, it is possible to restrain the combustion of the organic solvent and to eliminate the heat of reaction when the reaction temperature is raised.

It is also discovered that water contained in the reaction mixture eliminates the heat of reaction more effectively and restrains the combustion of the organic solvent, thereby achieving improved yield of target product.

In addition, the above-mentioned catalysts are also effective as oxidation catalyst for the production of diaryldicarboxylic acids from dialkyl-substituted diaryl compounds.

Namely, the present invention consists in a method of producing naphthalenedicarboxylic acids of general formula (II)

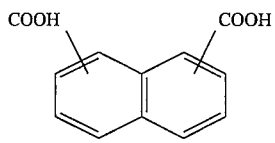

by oxidizing dialkyl-substituted naphthalene of general formula (I)

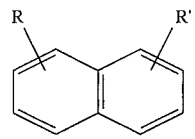

(wherein R and R' represent an alkyl group selected from the group consisting of methyl, ethyl and isopropyl groups, and wherein R and R' can be the same or different from each other),
with a gas containing molecular oxygen under liquid phase conditions, and a method of producing diaryldicarboxylic acids of general formula (IV)

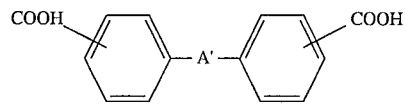

(wherein A' represents either direct bonding, O, $SO_2$ or CO) from dialkyl-substituted diaryl compounds of general formula (III)

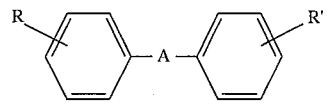

(wherein A represents either direct bonding, O, S, $SO_2$, CO or $CH_2$, R and R' respectively represent an alkyl group of 1 to 6 carbons or an alicyclic hydrocarbon group, and wherein R and R' can be the same or different from each other),
both the methods using a catalyst whose active components are copper and bromine in an acetic acid solvent (the ratio of copper to bromine in numbers of atoms is 1:a, a being in the range of $100<a\leq10000$).

The present invention uses a catalyst whose active components are copper and bromine, and preferably uses catalysts of the following compositions:

1) A catalyst whose active components are copper, bromine and manganese, wherein the ratio of copper to bromine and manganese in numbers of atoms is 1:a:b, a being in the range of $100<a\leq10000$, b being in the range of $0.1\leq b\leq10000$.

2) A catalyst whose active components are copper, bromine, manganese and heavy metal, wherein the ratio of copper to bromine, manganese and heavy metal in numbers of atoms is 1:a:b:c, a being in the range of $100<a\leq10000$, b being in the range of $0.1\leq b\leq10000$, c being in the range of $0.1\leq c\leq10000$.

3) A catalyst whose active components are copper, bromine and heavy metal, wherein the ratio of copper to bromine and heavy metal in numbers of atoms is 1:a:c, a being in the range of $100<a\leq10000$, c being in the range of $0.1\leq c\leq10000$.

4) A catalyst whose active components are copper, bromine and amine compound, wherein the ratio copper:bromine:amine compound, that is the ratio of the number of atoms of copper to the number of atoms of bromine and the number of moles of amine compound, is 1:a:d, a being in the range of $100<a\leq10000$, d being in the range of $0.1\leq d\leq10000$.

5) A catalyst whose active components are copper, bromine, amine compound and heavy metal, wherein the ratio copper:bromine:amine compound:heavy metal, that is the ratio of the number of atoms of copper to the number of atoms of bromine, the number of moles of amine compound and the number of atoms of heavy metal, is 1:a:d:e, a being in the range of 100<a≦10000, and d being in the range of 0.1≦d≦10000, e being in the range of 0.1≦e≦10000.

As for copper constituting these catalysts, for example, the following are listed: salts formed from copper and carboxylic acids such as formic acid, acetic acid and naphthenic acid; organic compounds such as acetylacetonate complex with copper, etc.; and inorganic compounds formed from copper and hydroxide, oxide, chloride, bromide, nitrate, sulfate or the like. These copper salts can be either anhydrous salts or hydrate salts.

Regarding bromine, a variety of bromine compounds, such as hydrogen bromide, ammonium bromide and metallic bromide, are listed.

For heavy metal in the catalysts of 2), 3) and 5), at least one kind of metallic element selected from the group consisting of vanadium, manganese, iron, cobalt, nickel, palladium and cerium, is used, and most preferably cobalt and manganese are used. Further, for the compounds, salts similar to the above-mentioned copper compounds is used.

Regarding amine compounds in the catalysts of 4) and 5), for example, the following are listed: heterocyclic amine compounds, such as pyridine, pyrazine, piperazine, picoline, lutidine, and quinoline; and alkyl amines having liquid state at room temperature, such as ethylenediamine, monopropylamine, dipropylamine, monobutylamine and dibutylamine. By considering the stability under oxidation conditions, pyridine, pyrazine, quinoline are listed as suitable amine compounds, and the most suitable one is pyridine.

The reaction according to the present invention is carried out in an organic solvent. Economically, and by considering the stability with respect to oxidation, a pure acetic acid solvent is used most preferably. However, the acetic acid solvent may be mixed with an aromatic solvent such as benzene, and aliphatic monocarboxylic acids for example propionic acid if necessary.

As for the amount of water in the reaction mixture, in the case when acetic acid is used as a solvent, it is preferable to contain water equal to 2 to 30 weight percent of the acetic acid. If the amount of water exceeds 30 weight percent, the catalytic activity is lowered, causing an increase of by-products and corrosion of a device.

In the present invention, the dialkyl-substituted diaryl compounds of formula (III) illustrated above is oxidized to the diaryldicarboxylic acid of formula (IV) also illustrated. R and R' in formula (III) are oxidized to a COOH group. When A in formula (III) is S or $CH_2$, S and $CH_2$ are also oxidized to $SO_2$ and CO respectively. In the mean time, if A in this formula is either direct bonding, O, $SO_2$, or CO, A' in formula (IV) is the same as A.

As dialkyl-substituted diaryl compounds, dialkyl-substituted diaryl having an alkyl group of 1 to 6 carbons and alicyclic hydrocarbon group as a substitution group are listed. More specifically, the following will give some examples of dialkyl-substituted diaryl compound and obtainable diaryldicarboxylic acid: 4,4'-dimethylbiphenyl and 4,4'-biphenyldicarboxylic acid; 3,3'-dimethylbiphenyl and 3,3'-biphenyldicarboxylic acid; 3,4'-dimethylbiphenyl and 3,4'-biphenyldicarboxylic acid; 4,4'-diethylbiphenyl and 4,4'-biphenyldicarboxylic acid; 3,3'-diethylbiphenyl and 3,3'-biphenyldicarboxylic acid; 3,4'-diethylbiphenyl and 3,4'-biphenyldicarboxylic acid; 4,4'-diisopropylbiphenyl and 4,4'-biphenyldicarboxylic acid; 3,3'-diisopropylbiphenyl and 3,3'-biphenyldicarboxylic acid; 3,4'-diisopropylbiphenyl and 3,4'-biphenyldicarboxylic acid; 4,4'-dicyclohexylbiphenyl and 4,4'-biphenyldicarboxylic acid; 4,4'-dimethyldiphenyl ether and 4,4'-diphenyl ether dicarboxylic acid; 4,4'-dimethylbenzophenone and 4,4'-benzophenone dicarboxylic acid; 3,3'-dimethylbenzophenone and 3,3'-benzophenone dicarboxylic acid; 4,4'-dimethyldiphenyl sulfone and 4,4'-diphenylsulfone dicarboxylic acid; 4,4'-dimethyldiphenyl sulfide and 4,4'-diphenylsulfone dicarboxylic acid; and bis(4-methylphenyl) methane and 4,4'-benzophenone dicarboxylic acid.

The production of naphthalenedicarboxylic acids and diaryldicarboxylic acids according to the present invention is carried out through either of the following two methods, (i) and (ii).

In method (i), naphthalenedicarboxylic acids or diaryldicarboxylic acids is produced through the following process: placing a predetermined amount of solvent, of starting material and of catalyst into a reaction vessel; suppling a gas containing molecular oxygen to the reaction vessel, stirring the mixture under a pressure of the gas at a predetermined temperature, and carrying out a reaction.

In method (ii), naphthalenedicarboxylic acids or diaryldicarboxylic acids is produced through the following process: placing a predetermined amount of solvent and of catalyst into a reaction vessel; suppling a gas containing molecular oxygen to the reaction vessel while adding a starting material to the reaction vessel successively or intermittently, stirring the mixture under a pressure of the gas at a predetermined temperature, and carrying out a reaction. Here, the reaction may be carried out by introducing a part of the starting material into the reaction vessel in advance, or the reaction may continuously proceed by withdrawing some parts of the produced naphthalenedicarboxylic acids or diaryldicarboxylic acids from the reaction mixture.

As for the amount of catalyst used in the present invention, it equals 0.01 weight percent to 20 weight percent of the solvent, and more preferably from 0.5 weight percent to 5 weight percent thereof. A catalyst concentration lower than this range will not achieve a good activation, and a catalyst concentration higher than this range will deteriorate its solubility and increase the formation of by-products, and therefore it is undesirable to use a catalyst beyond this range.

Regarding a gas containing molecular oxygen, although air is the most suitable source industrially, oxygen and a mixed gas formed by diluting oxygen with an intert gas may also be used.

In the case of using air, it is desirable to set the reaction temperature between 150° C. and 250° C., i.e. in this temperature range the reaction can promptly proceed and the formation of undesirable by-products such as tar-like substances and carbide is restrained.

Meanwhile, in the case of using air, suitable reaction pressures range from 3 kg/cm² to 50 kg/cm² in which the mixture is maintained in liquid phase, and the most preferable reaction pressures range from 10 kg/cm² to 40 kg/cm².

The following examples will explain the present invention in more detail, however the present invention is not restricted to these examples.

DETAILED DESCRIPTION OF THE PREFERRED EMBODIMENTS

The conversion of starting materials, the yield of naphthalenedicarboxylic acids, the yield of trimellitic acid (hereinafter referred to as TMA) which is an undesirable by-product, and the yield of diaryldicarboxylic acid in EXAMPLES and COMPARATIVE EXAMPLES were determined based on the following definitions.

$$\text{Conversion (\%)} = \frac{\text{number of moles of consumed starting material}}{\text{number of moles of supplied starting material}} \times 100$$

$$\text{NDA yield (\%)} = \frac{\text{number of moles of produced NDA}}{\text{number of moles of supplied starting material}} \times 100$$

$$\text{TMA yield (\%)} = \frac{\text{number of moles of produced TMA}}{\text{number of moles of supplied starting material}} \times 100$$

$$\text{Yield of diaryldicarboxylic acid (\%)} = \frac{\text{number of moles of produced diaryldicarboxylic acid}}{\text{number of moles of supplied starting material}} \times 100$$

EXAMPLE 1

In this example, a reaction was carried out according to method (ii) described above. More specifically, 300 g of acetic acid, and 0.1 g of copper acetate [$Cu(OAc)_2$] and 6 g of KBr as catalyst were placed into a titanium made 1 l autoclave equipped with a stirrer, a condenser, a gas blowing tube, a starting material supplying line and pressure-control valve. The mixture was heated to 200° C. and then pressurized to 30 kg/cm² with air.

Next, while supplying a volume of air enough for oxidation to the autoclave and while controlling the internal pressure of the autoclave at 30 kg/cm², 80.0 g of 2,6-diisopropylnaphthalene (hereinafter referred to as 2,6-DIPN) was added to the mixture in three hours stepwise to commence the reaction. Only air was supplied to therein for another one hour to proceed the reaction, and then the reaction was terminated.

The reaction product was analyzed with liquid chromatography. The analysis resulted in 100 percent conversion of 2,6-DIPN, 71 percent yield of 2,6-NDA and 24 percent yield of TMA as shown in Table 2.

EXAMPLES 2 TO 16

Here, reactions were carried out under the same conditions as in EXAMPLE 1, except that the components and composition of catalyst were respectively changed as shown in Table 1 and the reaction temperature and pressure were also changed as shown in Table 2. The reaction conditions and results are respectively shown in Table 1 and Table 2.

As is clear from the results of EXAMPLES 1 to 16, high yields of 2,6-NDA, at least 71 percent, were almost achieved with small amounts of catalyst not greater than 15 percent of the amount of the starting material. Thus, the yield of 2,6-NDA was improved with reduced amounts of catalyst compared with conventional cases.

The results show that at least one kind of heavy metallic element selected from the group consisting of vanadium, manganese, iron, cobalt, nickel, palladium and cerium can be used as heavy metal in catalyst, and more preferably cobalt and manganese will be used.

COMPARATIVE EXAMPLE 1

With the use of a well known catalyst described in the prior art, i.e. the catalyst comprising manganese and bromine, a reaction was carried out under the same conditions as in EXAMPLE 1. The reaction conditions and results are respectively presented in Table 5 and Table 6.

As is clear from the results, copper is an essential component for the catalyst of the present invention.

COMPARATIVE EXAMPLE 2

Except for changes in the composition ratio of the catalyst, reaction temperature and the reaction time, a reaction was carried out under the same conditions as in EXAMPLE 1. The reaction conditions and results are respectively presented in Table 5 and Table 6.

COMPARATIVE EXAMPLE 3

Except for changes in the composition ratio of the catalyst and the reaction temperature, a reaction was carried out under the same conditions as in EXAMPLE 2. The reaction conditions and results are respectively presented in Table 5 and Table 6.

EXAMPLE 17

A reaction was carried out under the same conditions as in EXAMPLE 12, except that an acetic acid solution containing a 5 weight percent of water was used as solvent instead of acetic acid. The yield of 2,6-NDA, of TMA and the recovery of acetic acid were 85 percent, 12 percent and 95 percent, respectively.

EXAMPLE 18

A reaction was carried out under the same conditions as in EXAMPLE 16, except that an acetic acid solution containing a 10 weight percent of water was used as solvent instead of acetic acid. The yield of 2,6-NDA, of TMA and the recovery of acetic acid were 88 percent, 8 percent and 97 percent, respectively.

The results of EXAMPLES 17 and 18 show that the solutions containing water restrain the formation of TMA as well as the combustion of acetic acid.

EXAMPLES 19 TO 22

With the use of dialkyl-substituted naphthalenes other than 2,6-diisopropylnaphthalene as starting material, naphthalenedicarboxylic acids were produced.

A catalyst comprising copper, bromine and manganese was used in EXAMPLES 19 and 20, and a catalyst comprising copper, bromine, manganese and other heavy metal were used in EXAMPLES 21 and 22. The starting material was varied as shown in Table 4, and 250 g of acetic acid was used as solvent. Except for these differences, reactions were carried out under the same conditions as in EXAMPLE 1. The reaction conditions and results are respectively presented in Table 3 and Table 4.

EXAMPLE 23

A catalyst comprising copper, bromine, pyridine and manganese was used instead of the catalyst in EXAMPLE 21, and o-dichlorobenzene was used as solvent. Except for these differences, a reaction was carried out under the same conditions as in EXAMPLE 21. The reaction conditions and results are respectively shown in Table 3 and Table 4.

EXAMPLE 24

300 g of acetic acid as solvent, and 0.1 g of copper acetate [$Cu(OAc)_2 \cdot H_2O$] and 6 g of potassium bromide as catalyst were placed into a titanium made autoclave (1 l) equipped with a stirrer, a condenser, a gas blowing tube, a starting material supplying line and a pressure-control valve. The mixture was heated to 180° C. and then pressurized to 30 kg/cm$^2$ with air. Next, while supplying air to the autoclave at a rate of 200 l/hr and while controlling the internal pressure of the autoclave at 30 kg/cm$^2$, 80.0 g of 4,4'-diisopropylbiphenyl was added to the mixture in three hours stepwise. Only air was supplied for another one hour to proceed a reaction, and then the reaction was terminated.

The reaction product was analyzed with liquid chromatography. The analysis resulted in 100 percent conversion of 4,4'-diisopropylbiphenyl and 85 percent yield of 4,4'-biphenyldicarboxylic acid as shown in Table 8.

The amount of catalyst used was equivalent to 7.6 weight percent of the starting material.

EXAMPLES 25 TO 38

Reactions were carried out under the same conditions as in EXAMPLE 24, except that the catalyst and reaction temperature were respectively varied as shown in Tables 7 and 8. The respective results are presented in Table 8.

EXAMPLES 24 to 38 achieved high yields of 4,4'-biphenyldicarboxylic acid, at least 85 percent, with the use of small amounts of catalyst which are less than 15 weight percent of the starting material. Thus, it is clear from the results that the yield of 4,4'-biphenyldicarboxylic acid is improved with reduced amounts of catalyst compared to the prior art.

When manganese, iron, nickel, palladium and cerium were used as the components of the catalyst, a slightly colored crude cake was resulted after the reaction. Meanwhile, when cobalt and vanadium were used, the resulting crude cake was light yellow.

EXAMPLE 39

4,4'-dimethylbiphenyl was used as starting material instead of 4,4'-diisopropylbiphenyl, and reaction temperature, the composition of catalyst and the amount of catalyst were respectively varied as shown in Table 9 and Table 10. Except for these differences, a reaction was carried out under the same conditions as in EXAMPLE 24. The amount of catalyst used was equivalent to 3.8 weight percent of the starting material. The results are shown in Table 10.

EXAMPLE 40

4,4'-dimethylbiphenyl was used as starting material instead of 4,4'-diisopropylbiphenyl, and 0.01 g of copper acetylacetonate [$Cu(AA)_2$], 0.57 g of ammonium bromide and 1.5 g of cobalt acetate [$Co(OAc)_2 \cdot 4H_2O$] as catalyst were used. Except for these differences, a reaction was carried out under the same conditions as in EXAMPLE 24. The amount of catalyst used was equivalent to 3.5 weight percent of the starting material. The reaction conditions and results are respectively shown in Table 9 and Table 10.

EXAMPLE 41

A reaction was carried out under the same conditions as in EXAMPLE 39, except that 4,4'-diethylbiphenyl was used as starting material instead of 4,4'-dimethylbiphenyl and that reaction temperature was 180° C. The reaction conditions and results are respectively shown in Table 9 and Table 10.

EXAMPLE 42

A reaction was carried out under the same conditions as in EXAMPLE 41, except that 4,4'-diethyldiphenyl ether was used as starting material instead of 4,4'-dimethylbiphenyl and that the composition of catalyst was changed as shown in FIG. 9. The reaction conditions and results are respectively shown in Table 9 and Table 10.

EXAMPLE 43

A reaction was carried out under the same conditions as in EXAMPLE 41, except that 4,4'-diethyldiphenyl sulfone was used as starting material instead of 4,4'-dimethylbiphenyl. The reaction conditions and results are respectively shown in Table 9 and Table 10.

EXAMPLE 44

A reaction was carried out under the same conditions as in EXAMPLE 39, except that 4,4'-dimethylbenzophenone was used as starting material instead of 4,4'-dimethylbiphenyl. The reaction conditions and results are respectively shown in Table 9 and Table 10.

EXAMPLES 39 to 44 achieved high yields, at least 84 percent, of 4,4'-biphenyldicarboxylic acid with the use of small amounts of catalyst which were respectively equivalent to 3.5 weight percent and 3.8 weight percent of the starting material when 4,4'-diethylbiphenyl, 4,4'-dimethyldiphenyl ether, 4,4'-dimethyldiphenyl sulfone and 4,4'-dimethylbenzophenone were used as starting material. Thus, the results show that the yield of 4,4'-biphenyldicarboxylic acid is improved with reduced amounts of catalyst compared with the prior art.

EXAMPLES 45 AND 46

The catalysts given in Table 9, the isomer of 4,4'-diisopropylbiphenyl as starting material and 250 g of acetic acid as solvent were used. Except for these changes, reactions were carried out under the same conditions as in EXAMPLE 24. The reaction conditions and results are respectively presented in Table 9 and Table 10.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

TABLE 1

| Example No. | Components of Catalyst (g) | | | | Composition (atom ratio) | | | |
|---|---|---|---|---|---|---|---|---|
| | | | | | Cu | Br | Mn | Heavy Metal |
| 1 | Cu(OAc)$_2$H$_2$O, (0.1) | KBr, (6.0) | — | — | 1 | 101 | — | — |
| 2 | Cu(OAc)$_2$H$_2$O, (0.1) | KBr, (6.0) | — | Co(OAc)$_2$4H$_2$O (3.0) | 1 | 101 | — | 24 |
| 3 | Cu(OAc)$_2$H$_2$O, (0.1) | KBr, (6.0) | Mn(OAc)$_2$4H$_2$O (3.0) | — | 1 | 101 | 24 | — |
| 4 | Cu(OAc)$_2$H$_2$O, (0.1) | KBr, (6.0) | — | VO(AA)$_3$ (1.0) | 1 | 101 | — | 8 |
| 5 | Cu(OAc)$_2$H$_2$O, (0.1) | KBr, (6.0) | — | Fe(AA)$_2$ (3.0) | 1 | 101 | — | 17 |
| 6 | Cu(OAc)$_2$H$_2$O, (0.1) | KBr, (6.0) | — | Pd(OAc)$_2$ (0.1) | 1 | 101 | — | 0.8 |
| 7 | Cu(OAc)$_2$H$_2$O, (0.05) | KBr, (5.0) | — | Ce(OAc)$_3$H$_2$O (3.0) | 1 | 168 | — | 37 |
| 8 | Cu(OAc)$_2$H$_2$O, (0.05) | NH$_4$Br, (4.0) | — | Co(OAc)$_2$4H$_2$O (3.0) | 1 | 164 | — | 48 |
| 9 | Cu(AA)$_2$, (0.05) | NH$_4$Br, (4.0) | — | Co(OAc)$_2$4H$_2$O (3.0) | 1 | 218 | — | 64 |
| 10 | Cu(AA)$_2$, (0.05) | KBr, (5.0) | Mn(OAc)$_2$4H$_2$O (6.0) | — | 1 | 223 | 127 | — |
| 11 | Cu(AA)$_2$, (0.05) | KBr, (5.0) | — | Co(AA)$_3$ (3.0) | 1 | 223 | — | 43 |
| 12 | Cu(AA)$_2$, (0.02) | KBr, (5.0) | — | Co(AA)$_3$ (6.0) | 1 | 556 | — | 87 |
| 13 | Cu(AA)$_2$, (0.01) | KBr, (5.0) | Mn(AA)$_2$ (6.0) | — | 1 | 556 | 614 | — |
| 14 | Cu(AA)$_2$, (0.02) | KBr, (5.0) | — | Ni(AA)$_2$ (3.0) | 1 | 556 | — | 154 |
| 15 | Cu(OAc)$_2$H$_2$O, (0.005) | KBr, (5.0) | Mn(OAc)$_2$4H$_2$O (6.5) | — | 1 | 1681 | 1061 | — |
| 16 | Cu(OAc)$_2$H$_2$O, (0.001) | KBr, (5.0) | Mn(OAc)$_2$4H$_2$O (10.0) | — | 1 | 8403 | 8163 | — |

Ac: acetyl group, and AA: acetylacetonate group.

TABLE 2

| Example No. | Reaction Conditions | | | Conversion (%) | Yield (%) | | Recovery of Acetic Acid (%) |
|---|---|---|---|---|---|---|---|
| | Temperature (°C.) | Time (hr) | Pressure (kg/cm$^2$) | | 2,6-NDA | TMA | |
| 1 | 200 | 4 | 30 | 100 | 71 | 24 | 88 |
| 2 | 200 | 4 | 30 | 100 | 81 | 14 | 89 |
| 3 | 210 | 4 | 30 | 100 | 83 | 13 | 87 |
| 4 | 200 | 4 | 30 | 100 | 76 | 13 | 86 |
| 5 | 200 | 4 | 30 | 100 | 73 | 23 | 90 |
| 6 | 200 | 4 | 30 | 100 | 72 | 12 | 87 |
| 7 | 200 | 4 | 30 | 100 | 75 | 21 | 90 |
| 8 | 200 | 4 | 30 | 100 | 82 | 13 | 91 |
| 9 | 200 | 4 | 30 | 100 | 82 | 15 | 88 |
| 10 | 220 | 4 | 30 | 100 | 86 | 12 | 90 |
| 11 | 210 | 4 | 30 | 100 | 81 | 16 | 91 |
| 12 | 210 | 4 | 20 | 100 | 83 | 15 | 90 |
| 13 | 210 | 4 | 20 | 100 | 88 | 9 | 93 |
| 14 | 210 | 4 | 30 | 100 | 79 | 18 | 94 |
| 15 | 230 | 4 | 30 | 100 | 84 | 15 | 93 |
| 16 | 220 | 4 | 30 | 100 | 85 | 10 | 95 |

300 g of acetic acid and 80 g of 2,6-diisopropylnaphthalene were respectively used as solvent and starting material in each example.
2,6-NDA: 2,6-naphthalenedicarboxylic acid, and TMA: trimellitic acid.

TABLE 3

| Example No. | Components of Catalyst (g) | | | | Composition (atom ratio) | | | | |
|---|---|---|---|---|---|---|---|---|---|
| | | | | | Cu | Br | Mn | Heavy Metal | Y* |
| 19 | $Cu(OAc)_2H_2O$, (0.05) | KBr, (3.0) | $Mn(OAc)_24H_2O$ (5.0) | | 1 | 101 | 82 | — | — |
| 20 | $Cu(OAc)_2H_2O$, (0.05) | KBr, (3.0) | $Mn(OAc)_24H_2O$ (5.0) | | 1 | 101 | 82 | — | — |
| 21 | $Cu(OAc)_2H_2O$, (0.05) | KBr, (3.6) | $Mn(OAc)_24H_2O$ (5.0) | $Ni(AA)_2$ (1.0) | 1 | 101 | 82 | 15 | — |
| 22 | $Cu(OAc)_2H_2O$, (0.05) | KBr, (3.0) | $Mn(OAc)_24H_2O$ (5.0) | $Ni(AA)_2$ (1.0) | 1 | 101 | 82 | 15 | — |
| 23 | $Cu(OAc)_2H_2O$, (0.02) | KBr, (3.0) | $Mn(OAc)_24H_2O$ (3) | Py (2.5) | 1 | 252 | 122 | — | 316 |

Y: amine compound, Py: pyridine, Ac: acetyl group, and *: number of moles.

TABLE 4

| Example No. | Solvent (g) | Starting Material (g) | Reaction Conditions | | | Conversion (%) | Yield (%) | Recovery of Acetic Acid (%) |
|---|---|---|---|---|---|---|---|---|
| | | | Temperature (°C.) | Time (hr) | Pressure (kg/cm²) | | | |
| 19 | AcA | 2,7-DIPN (60) | 200 | 4 | 30 | 100 | 2,7-NDA (70) | 87 |
| 20 | AcA | 1,4-DIPN (60) | 200 | 4 | 30 | 100 | 1,4-NDA (68) | 91 |
| 21 | AcA | 2,7-DIPN (60) | 200 | 4 | 30 | 100 | 2,7-NDA (72) | 90 |
| 22 | AcA | 1,4-DIPN (60) | 200 | 4 | 30 | 100 | 1,4-NDA (69) | 93 |
| 23 | DCB | 2,7-DIPN (60) | 200 | 4 | 30 | 100 | 2,7-NDA (65) | — |

250 g of solvent was used in each example.
AcA: acetic acid, DCB: o-dichlorobenzene, DIPN: diisopropylnaphthalene, and NDA: naphthalenedicarboxylic acid.

TABLE 5

| Comparative Example No. | Components of Catalyst (g) | | | Composition (atom ratio) | | | |
|---|---|---|---|---|---|---|---|
| | | | | Cu | Br | Mn | Heavy Metal |
| 1 | — | KBr, (2.13) | $Mn(OAc)_24H_2O$ (2.20) | — | 100 | 100 | — |
| 2 | $Cu(OAc)_2H_2O$, (2.0) | KBr, (3.0) | | 1 | 2.5 | — | — |
| 3 | $Cu(OAc)_2H_2O$, (0.4) | KBr, (3.0) | $Co(OAc)_24H_2O$ (3.0) | 1 | 12.6 | — | 6.0 |

Ac: acetyl group.

TABLE 6

| Comparative Example No. | Reaction Conditions | | | Conversion (%) | Yield (%) | | Recovery of Acetic Acid (%) |
|---|---|---|---|---|---|---|---|
| | Temperature (°C.) | Time (hr) | Pressure (kg/cm²) | | 2,6-NDA | TMA | |
| 1 | 210 | 6 | 30 | 100 | 21 | 32 | — |
| 2 | 225 | 6 | 30 | 100 | 61 | 32 | 71 |
| 3 | 200 | 4 | 30 | 100 | 81 | 15 | 75 |

TABLE 7

| Example No. | Components of Catalyst (g) | | | | Composition (atom ratio) | | | |
|---|---|---|---|---|---|---|---|---|
| | | | | | Cu | Br | Mn | Heavy Metal |
| 24 | Cu(OAc)$_2$H$_2$O, (0.1) | KBr, (6.0) | — | — | 1 | 101 | — | — |
| 25 | Cu(OAc)$_2$H$_2$O, (0.1) | KBr, (6.0) | — | Co(OAc)$_2$4H$_2$O (3.0) | 1 | 101 | — | 24 |
| 26 | Cu(OAc)$_2$H$_2$O, (0.1) | KBr, (6.0) | Mn(OAc)$_2$4H$_2$O (3.0) | — | 1 | 101 | 24 | — |
| 27 | Cu(OAc)$_2$H$_2$O, (0.1) | KBr, (6.0) | — | VO(AA)$_3$ (1.0) | 1 | 101 | — | 8 |
| 28 | Cu(OAc)$_2$H$_2$O, (0.1) | KBr, (6.0) | — | Fe(AA)$_3$ (3.0) | 1 | 101 | — | 17 |
| 29 | Cu(OAc)$_2$H$_2$O, (0.1) | KBr, (5.0) | — | Pd(OAc)$_2$ (0.1) | 1 | 101 | — | 0.8 |
| 30 | Cu(OAc)$_2$H$_2$O, (0.05) | KBr, (5.0) | — | Ce(OAc)$_3$H$_2$O (3.0) | 1 | 168 | — | 37 |
| 31 | Cu(OAc)$_2$H$_2$O, (0.05) | NH$_4$Br, (4.0) | — | Co(OAc)$_2$4H$_2$O (3.0) | 1 | 164 | — | 48 |
| 32 | Cu(AA)$_2$, (0.05) | NH$_4$Br, (4.0) | — | Co(OAc)$_2$4H$_2$O (3.0) | 1 | 218 | — | 64 |
| 33 | Cu(AA)$_2$, (0.05) | KBr, (5.0) | Mn(OAc)$_2$4H$_2$O (6.0) | — | 1 | 223 | 127 | — |
| 34 | Cu(AA)$_2$, (0.05) | KBr, (5.0) | — | Co(AA)$_3$ (3.0) | 1 | 223 | — | 43 |
| 35 | Cu(AA)$_2$, (0.02) | KBr, (5.0) | — | Co(AA)$_3$ (6.0) | 1 | 556 | — | 87 |
| 36 | Cu(AA)$_2$, (0.01) | KBr, (5.0) | Mn(AA)$_3$ (6.0) | — | 1 | 556 | 614 | — |
| 37 | Cu(AA)$_2$, (0.02) | KBr, (5.0) | — | Ni(AA)$_2$ (3.0) | 1 | 556 | — | 154 |
| 38 | Cu(OAc)$_2$H$_2$O, (0.005) | KBr, (5.0) | Mn(OAc)$_2$4H$_2$O (6.5) | — | 1 | 1681 | 1061 | — |

TABLE 8

| Example No. | Reaction Conditions | | | | | Recovery of Acetic Acid (%) |
|---|---|---|---|---|---|---|
| | Temperature (°C.) | Time (hr) | Pressure (kg/cm$^2$) | Conversion (%) | Yield (%) | |
| 24 | 180 | 4 | 30 | 100 | 85 | 94 |
| 25 | 180 | 4 | 30 | 100 | 88 | 93 |
| 26 | 180 | 4 | 30 | 100 | 93 | 92 |
| 27 | 170 | 4 | 30 | 100 | 86 | 95 |
| 28 | 180 | 4 | 30 | 100 | 87 | 96 |
| 29 | 170 | 4 | 30 | 100 | 85 | 90 |
| 30 | 170 | 4 | 30 | 100 | 86 | 92 |
| 31 | 180 | 4 | 30 | 100 | 89 | 93 |
| 32 | 180 | 4 | 30 | 100 | 90 | 94 |
| 33 | 180 | 4 | 30 | 100 | 92 | 93 |
| 34 | 190 | 4 | 30 | 100 | 91 | 91 |
| 35 | 200 | 4 | 30 | 100 | 89 | 94 |
| 36 | 200 | 4 | 20 | 100 | 94 | 95 |
| 37 | 200 | 4 | 20 | 100 | 86 | 96 |
| 38 | 190 | 4 | 30 | 100 | 88 | 98 |

80 g of 4,4'-diisopropylbiphenyl was used as starting material and 300 g of acetic acid was used as solvent in each example

TABLE 9

| Example No. | Components of Catalyst (g) | | | | Composition (atom ratio) | | | |
| --- | --- | --- | --- | --- | --- | --- | --- | --- |
| | | | | | Cu | Br | Mn | Heavy Metal |
| 39 | Cu(OAc)$_2$H$_2$O, (0.01) | KBr, (0.75) | Mn(OAc)$_2$4H$_2$O (1.5) | — | 1 | 126 | 122 | — |
| 40 | Cu(AA)$_2$, (0.01) | NH$_4$Br, (0.57) | — | Co(OAc)$_2$4H$_2$O (1.5) | 1 | 154 | — | 120 |
| 41 | Cu(OAc)$_2$H$_2$O, (0.01) | KBr, (0.75) | Mn(OAc)$_2$4H$_2$O (1.5) | — | 1 | 126 | 122 | — |
| 42 | Cu(OAc)$_2$H$_2$O, (0.1) | KBr, (0.75) | — | Ce(OAc)$_3$H$_2$O (0.75) | 1 | 126 | — | 46 |
| 43 | Cu(OAc)$_2$H$_2$O, (0.01) | KBr, (0.75) | Mn(OAc)$_2$4H$_2$O (1.5) | — | 1 | 126 | 122 | — |
| 44 | Cu(OAc)$_2$H$_2$O, (0.01) | KBr, (0.75) | Mn(OAc)$_2$4H$_2$O (1.5) | — | 1 | 126 | 122 | — |
| 45 | Cu(OAc) H$_2$O, (0.01) | KBr, (0.75) | Mn(OAc)$_2$4H$_2$O (1.5) | — | 1 | 126 | 122 | — |
| 46 | Cu(OAc)$_2$H$_2$O, (0.01) | KBr, (3) | Mn(OAc)$_2$4H$_2$O (4.8) | — | 1 | 503 | 391 | — |

Ac: acetyl group, and AA: acetylacetonate group.

TABLE 10

| Example No. | Starting Material (g) | Reaction Conditions | | | Conversion (%) | Yield (%) | Recovery of Acetic Acid (%) |
| --- | --- | --- | --- | --- | --- | --- | --- |
| | | Temperature (°C.) | Time (hr) | Pressure (kg/cm$^2$) | | | |
| 39 | DMB (60) | 190 | 4 | 30 | 100 | 88 | 97 |
| 40 | DMB (60) | 180 | 4 | 30 | 100 | 90 | 98 |
| 41 | DEB (60) | 180 | 4 | 30 | 100 | 93 | 95 |
| 42 | DDE (60) | 180 | 4 | 30 | 100 | 94 | 98 |
| 43 | DDS (60) | 180 | 4 | 30 | 100 | 85 | 96 |
| 44 | DMBP (60) | 180 | 4 | 30 | 100 | 84 | 98 |
| 45 | 3,4'-DIPB (60) | 180 | 4 | 30 | 100 | 3,4'-BPDA (82) | 97 |
| 46 | 3,3'-DIPB (60) | 180 | 4 | 30 | 100 | 3,3'-BPDA (80) | 97 |

300 g of acetic acid was used as solvent in examples 39 to 44, and 250 g of acetic acid was used in examples 45 and 46. The yield in example 39 to 44 respectively represents the yield of 4,4'-biphenyldicarboxylic acid. DMB: 4,4'-dimethylbiphenyl, DEB: 4,4'-diethylbiphenyl, DDE: 4,4'-dimethyldiphenyl ether, DDS: 4,4'-dimethyldiphenyl sulfone, DMBP: 4,4'-dimethylbenzophenone, DIPB: 4,4'-diisopropylbiphenyl, and BPDA: biphenyldicarboxylic acid.

What is claimed is:

1. A method of producing naphthalenedicarboxylic acids of the formula

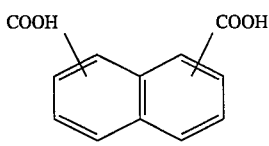

comprising:
oxidizing dialkyl-substituted naphthalene of the formula

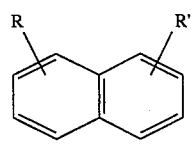

wherein R and R' respectively represent an alkyl group selected from the group consisting of methyl, ethyl and isopropyl groups, and wherein R and R' are the same or different from each other,
with a gas containing molecular oxygen under liquid phase conditions in the presence of a catalyst consisting essentially of copper, bromine and manganese in an organic solvent,
wherein the ratio of copper to bromine in the catalyst in numbers of atoms is 1:a, a being greater than 100.

2. The method of producing naphthalenedicarboxylic acids as defined in claim 1, wherein the dialkyl-substituted naphthalene is 2,6-diisopropylnaphthalene.

3. The method of producing naphthalenedicarboxylic acids as defined in claim 1, wherein the organic solvent comprises acetic acid.

4. The method of producing naphthalenedicarboxylic acids as defined in claim 1, wherein the ratio of the copper to the bromine in the catalyst in numbers of atoms is 1:a, a being in the range of 100<a≦10000.

5. The method of producing naphthalenedicarboxylic acids as defined in claim 4, wherein the dialkyl-substituted naphthalene is 2,6-diisopropylnaphthalene.

6. The method of producing naphthalenedicarboxylic acids as defined in claim 4, wherein the ratio of the copper to the bromine and the manganese in numbers of atoms is 1:a:b, a being in the range of $100<a\leq 10000$, b being in the range of $0.1\leq b\leq 10000$.

7. The method of producing naphthalenedicarboxylic acids as defined in claim 6, wherein the dialkyl-substituted naphthalene is 2,6-diisopropylnaphthalene.

8. The method of producing naphthalenedicarboxylic acids as defined in claim 1, wherein the oxidation reaction is carried out at a temperature between 150° C. and 250° C.

9. The method of producing naphthalenedicarboxylic acids as defined in claim 1, wherein the oxidation reaction pressure is at least 3 kg/cm².

10. The method of producing naphthalenedicarboxylic acids as defined in claim 1, wherein the oxidation reaction pressure is in the range of 3 kg/cm² to 50 kg/cm².

11. The method of producing naphthalenedicarboxylic acids as defined in claim 1, wherein the organic solvent comprises water.

12. A method of producing diaryldicarboxylic acids of the formula

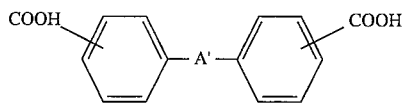

wherein A' represents either direct bonding, O, SO₂ or CO, comprising:

oxidizing a dialkyl-substituted diaryl compound of the formula

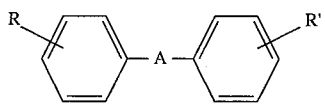

wherein A represents either direct bonding, O, S, SO₂, CO, or CH₂, and wherein R and R' respectively represent an alkyl group of 1 carbon to 6 carbons or an alicyclic hydrocarbon group, R and R' being the same or different from each other, with a gas containing molecular oxygen under liquid phase conditions in the presence of a catalyst consisting essentially of copper, bromine and manganese in an organic solvent, wherein the ratio of copper to bromine in the catalyst in numbers of atoms is 1:a, a being in the range of $100<a\leq 10000$.

13. The method of producing diaryldicarboxylic acids as defined in claim 12, wherein the dialkyl-substituted diaryl compound is 4,4'-diisopropylbiphenyl.

14. The method of producing diaryldicarboxylic acids as defined in claim 12, wherein the organic solvent comprises acetic acid.

15. The method of producing diaryldicarboxylic acids as defined in claim 12, wherein the ratio of the copper to the bromine and the manganese in numbers of atoms is 1:a:b, a being in the range of $100<a\leq 10000$, b being in the range of $0.1\leq b\leq 10000$.

16. The method of producing diaryldicarboxylic acids as defined in claim 15, wherein the dialkyl-substituted diaryl compound is 4,4'-diisopropylbiphenyl.

17. The method of producing naphthalenedicarboxylic acids as defined in claim 12, wherein the oxidation reaction is carried out at a temperature between 150° C. and 250° C.

18. The method of producing naphthalenedicarboxylic acids as defined in claim 12, wherein the oxidation reaction pressure is at least 3 kg/cm².

19. The method of producing naphthalenedicarboxylic acids as defined in claim 12, wherein the oxidation reaction pressure is in the range of 3 kg/cm² to 50 kg/cm².

20. The method of producing naphthalenedicarboxylic acids as defined in claim 12, wherein the organic solvent comprises water.

21. A method of producing naphthalenedicarboxylic acids of the formula

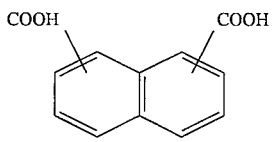

comprising:

oxidizing dialkyl-substituted naphthalene of the formula

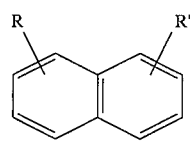

wherein R and R' respectively represent an alkyl group selected from the group consisting of methyl, ethyl and isopropyl groups, and wherein R and R' are the same or different from each other, with a gas containing molecular oxygen under liquid phase conditions in the presence of a catalyst consisting essentially of copper, bromine, manganese and an amine component in an organic solvent, wherein the ratio of copper to bromine and amine compound in the catalyst in numbers of atoms is 1:a:d, a being greater than 100, and d being in the range of $0.1<d\leq 10,000$.

22. The method of producing naphthalenedicarboxylic acids as defined in claim 21, wherein the amine compound is pyridine.

23. A method of producing naphthalenedicarboxylic acids of the formula

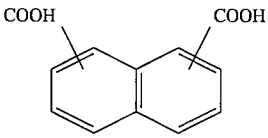

comprising:

oxidizing dialkyl-substituted naphthalene of the formula

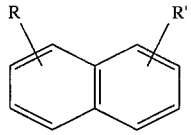

wherein R and R' respectively represent an alkyl group selected from the group consisting of methyl, ethyl and isopropyl groups, and wherein R and R' are the same or different from each other, with a gas containing molecular oxygen under liquid phase conditions in the presence of a catalyst consisting essentially of copper, bromine, manganese and at least one heavy metal component selected from the group consisting of vanadium, iron, nickel, palladium and cerium in an organic solvent, wherein the ratio of copper to bromine and heavy metal element in the catalyst in numbers of atoms is 1:a:c, a being greater than 100, and c being in the range of $0.1 \leq c \leq 10{,}000$.

24. The method of producing naphthalenedicarboxylic acids according to claim 23, wherein the ratio of copper to bromine and manganese in the catalyst in numbers of atoms is 1:a:b, a being in the range of $100 < a \leq 10{,}000$, and b being in the range of $0.1 \leq b \leq 10{,}000$.

25. A method of producing diaryldicarboxylic acids of the formula

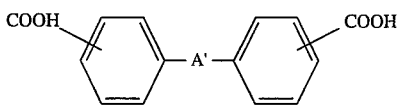

wherein A' represents either direct bonding, O, $SO_2$ or CO, comprising:

oxidizing a dialkyl-substituted diaryl compound of the formula

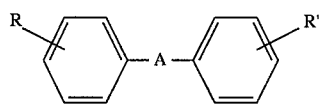

wherein A represents either direct bonding, O, S, $SO_2$, CO, or $CH_2$, and wherein R and R' respectively represent an alkyl group of 1 carbon to 6 carbons or an alicyclic hydrocarbon group, R and R' being the same or different from each other, with a gas containing molecular oxygen under liquid phase conditions in the presence of a catalyst consisting essentially of copper, bromine, manganese and an amine compound in an organic solvent, wherein the ratio of copper to bromine and amine compound in the catalyst in numbers of atoms is 1:a:d, a being in the range of $100 < a \leq 10000$, and d being in the range of $0.1 \leq d \leq 10{,}000$.

26. The method of producing diaryldicarboxylic acids as defined in claim 25, wherein the amine compound is pyridine.

27. A method of producing diaryldicarboxylic acids of the formula

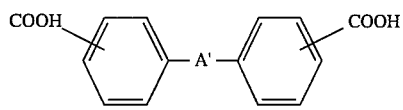

wherein A' represents either direct bonding, O, $SO_2$ or CO, comprising:

oxidizing a dialkyl-substituted diaryl compound of the formula

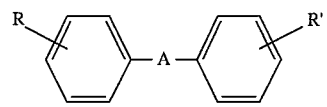

wherein A represents either direct bonding, O, S, $SO_2$, CO, or $CH_2$, and wherein R and R' respectively represent an alkyl group of 1 carbon to 6 carbons or an alicyclic hydrocarbon group, R and R' being the same or different from each other, with a gas containing molecular oxygen under liquid phase conditions in the presence of a catalyst consisting essentially of copper, bromine, manganese and at least one heavy metal component selected from the group consisting of vanadium, iron, nickel, palladium and cerium in an organic solvent, wherein the ratio of copper to bromine and heavy metal element in the catalyst in numbers of atoms is 1:a:c, a being in the range of $100 < a \leq 10000$, and c being in the range of $0.1 \leq c \leq 10{,}000$.

28. The method of producing diaryldicarboxylic acids according to claim 27, wherein the ratio of copper to bromine and manganese in the catalyst in numbers of atoms is 1:a:b, a being in the range of $100 < a \leq 10{,}000$, and b being in the range of $0.1 \leq b \leq 10{,}000$.

* * * * *